United States Patent [19]

Ueda et al.

[11] 4,411,900
[45] Oct. 25, 1983

[54] BENZHYDRYLPIPEROZINYL THIAZOLE DERIVATIVES AND PHARMACEUTICAL COMPOSITION COMPRISING THE SAME

[75] Inventors: Ikuo Ueda, Toyonaka; Daizou Morino, Matsubara; Koichi Takimoto, Osaka, all of Japan

[73] Assignee: Fujisawa Pharmaceutical Co., Ltd., Osaka, Japan

[21] Appl. No.: 215,372

[22] Filed: Dec. 11, 1980

[30] Foreign Application Priority Data

Jan. 3, 1980 [GB] United Kingdom ............... 8000162

[51] Int. Cl.$^3$ ............... C07D 295/02; A61K 31/495
[52] U.S. Cl. .................... 424/250; 544/367; 260/245.5; 548/203; 548/205; 424/270
[58] Field of Search ............... 544/367; 424/250

[56] References Cited

U.S. PATENT DOCUMENTS

| | | | |
|---|---|---|---|
| 2,543,972 | 3/1951 | Hultquist et al. .................. | 544/368 |
| 2,909,523 | 10/1959 | Bach et al. ........................ | 424/250 |
| 3,362,956 | 1/1968 | Archer ................................ | 544/367 |
| 3,489,757 | 1/1970 | Koppe et al. ...................... | 544/368 |
| 3,491,098 | 1/1970 | Archer ................................ | 424/250 |
| 3,491,098 | 1/1970 | Archer ................................ | 424/250 |
| 3,519,637 | 7/1970 | Nutley ................................ | 424/250 |
| 3,631,043 | 12/1971 | Regnier et al. .................... | 544/367 |
| 3,632,587 | 1/1972 | Hollowood et al. ............... | 424/250 |
| 3,956,328 | 5/1976 | Irikura ................................ | 424/250 |

FOREIGN PATENT DOCUMENTS

| | | | |
|---|---|---|---|
| 2012667 | 10/1970 | Fed. Rep. of Germany ...... | 424/250 |
| 48-93379 | 1/1973 | Japan .................................. | 544/367 |
| 1240648 | 7/1971 | United Kingdom ............... | 424/250 |
| 1326833 | 8/1973 | United Kingdom ............... | 424/250 |
| 1382887 | 2/1975 | United Kingdom ............... | 424/250 |
| 1382916 | 2/1975 | United Kingdom ............... | 424/250 |
| 1405365 | 9/1975 | United Kingdom ............... | 424/250 |

Primary Examiner—Donald G. Daus
Assistant Examiner—S. A. Gibson
Attorney, Agent, or Firm—Oblon, Fisher, Spivak, McClelland & Maier

[57] ABSTRACT

Benzhydrylpiperazinyl Thiazole compounds of the formula

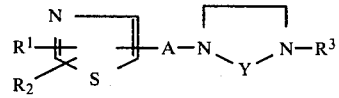

wherein
$R^1$ is hydrogen, amino, or mono- or di- substituted amino, in which the substituent is selected from lower alkyl, acyl and di(lower)alkylaminomethylene,
$R^2$ is hydrogen, halogen, lower alkyl or aryl,
$R^3$ is ar(lower)alkyl optionally substituted by halogen,
A is lower alkylene optionally interrupted by a sulfur atom, and
Y is $C_1$-$C_3$ alkylene,
having antiallergic activity.

18 Claims, No Drawings

BENZHYDRYLPIPEROZINYL THIAZOLE DERIVATIVES AND PHARMACEUTICAL COMPOSITION COMPRISING THE SAME

The present invention relates to novel thiazole derivatives and pharmaceutically acceptable salts thereof. More particularly, it relates to novel thiazole derivatives and pharmaceutically acceptable salts thereof which have antiallergic activities, to processes for the preparation thereof, to pharmaceutical composition comprising the same, and to a method of using the same therapeutically in the treatment of allergic symptoms in human being and animals.

Accordingly, it is one object of the present invention to provide thiazole derivatives and pharmaceutically acceptable salts thereof, which are useful as antiallergic agents.

Another object of the present invention is to provide processes for the preparation of thiazole derivatives and pharmaceutically acceptable salts thereof.

A further object of the present invention is to provide pharmaceutical composition comprising, as an active ingredient, said thiazole derivative or its pharmaceutically acceptable salt.

Still further object of the present invention is to provide a method of using said thiazole derivative or its pharmaceutically acceptable salt in the treatment of allergic symptoms in human being and animals.

The object thiazole derivatives of the present invention are novel and can be represented by the following formula (I):

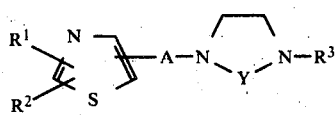

wherein
- $R^1$ is hydrogen, amino, or mono- or di-substituted amino, in which the substituent is selected from lower alkyl, acyl and di(lower)alkylaminomethylene,
- $R^2$ is hydrogen, halogen, lower alkyl or aryl,
- $R^3$ is ar(lower)alkyl optionally substituted by halogen,
- A is lower alkylene optionally interrupted by a sulfur atom, and
- Y is $C_1$-$C_3$alkylene.

With regard to the object compounds of the above formula (I), it is to be understood that the compounds (I) represent inclusively all of the possible optical and/or geometrical isomers due to the asymmetric carbon atom and carbon-nitrogen double bond (>C=N—) in the molecule of the compounds (I), and accordingly such optical and/or geometrical isomers are also included within the scope of the present invention.

As to the various definitions as indicated above, suitable illustrations and examples are explained in detail as follows.

The term "lower" is intended to mean 1 to 6 carbon atom(s), unless otherwise indicated.

In the definition of "mono- or di-substituted amino, in which the substituent is selected from lower alkyl, acyl and di(lower)alkylaminomethylene" for $R^1$, suitable examples of each substituent are as follows.

Suitable "lower alkyl" may include straight or branched one such as methyl, ethyl, propyl, isopropyl, butyl, isobutyl, tert-butyl, pentyl, hexyl and the like, in which the preferred one is $C_1$-$C_4$alkyl.

Suitable "acyl" may include an aliphatic acyl, an aromatic acyl, a heteroacyclic acyl and an aliphatic acyl substituted with aromatic or heterocyclic group(s).

The aliphatic acyl may include saturated or unsaturated, acyclic or cyclic ones, such as lower alkanoyl (e.g. formyl, acetyl, propionyl, butyryl, isobutyryl, valeryl, isovaleryl, pivaloyl, hexanoyl, etc.), lower alkanesulfonyl (e.g. methanesulfonyl, ethanesulfonyl, propanesulfonyl, butanesulfonyl, etc.), lower alkoxycarbonyl (e.g. methoxycarbonyl, ethoxycarbonyl, propoxycarbonyl, butoxycarbonyl, tert-butoxycarbonyl, etc.), N-lower alkylcarbamoyl (e.g. N-methylcarbamoyl, N-ethylcarbamoyl, N-propylcarbamoyl, etc.), lower alkoxalyl (e.g. methoxalyl, ethoxalyl, propoxalyl, etc.), lower alkenoyl (e.g. acryloyl, methacryloyl, crotonoyl, etc.), ($C_3$-$C_7$)-cycloalkanecarbonyl (e.g. cyclohexanecarbonyl, etc.), and the like.

The aromatic acyl may include aroyl (e.g. benzoyl, toluoyl, xyloyl, etc.), arenesulfonyl (e.g. benzenesulfonyl, tosyl, etc.), and the like.

The heterocyclic acyl may include heterocyclecarbonyl (e.g. furoyl, thenoyl, nicotinoyl, isonicotinoyl, thiazolylcarbonyl, thiadiazolylcarbonyl, tetrazolylcarbonyl, etc.), and the like.

The aliphatic acyl substituted with aromatic group(s) may include phenyl(lower)alkanoyl (e.g. phenylacetyl, phenylpropionyl, phenylhexanoyl, etc.), phenyl(lower)alkoxycarbonyl (e.g. benzyloxycarbonyl, phenethyloxycarbonyl, etc.), phenoxy(lower)alkanoyl (e.g. phenoxyacetyl, phenoxypropionyl, etc.), and the like.

The aliphatic acyl substituted with heterocyclic group(s) may include thienylacetyl, imidazolylacetyl, furylacetyl, tetrazolylacetyl, thiazolylacetyl, thiadiazolylacetyl, thienylpropionyl, thiadiazolylpropionyl, and the like.

These acyl groups may be further substituted with one or more suitable substituents such as lower alkyl (e.g. methyl, ethyl, propyl, isopropyl, butyl, pentyl, hexyl, etc.), halogen (e.g. chlorine, bromine, iodine, fluorine), lower alkoxy (e.g. methoxy, ethoxy, propoxy, isopropoxy, butoxy, pentyloxy, hexyloxy, etc.), lower alkylthio (e.g. methylthio, ethylthio, propylthio, isopropylthio, butylthio, pentylthio, hexylthio, etc.), nitro, and the like, and preferable acyl having such substituent(s) may be mono (or di or tri)halo(lower)alkanoyl (e.g. chloroacetyl, bromoacetyl, dichloroacetyl, trifluoroacetyl, etc.), mono (or di or tri)halo(lower)alkoxycarbonyl (e.g. chloromethoxycarbonyl, dichloromethoxycarbonyl, 2,2,2-tri-chloroethoxycarbonyl, etc.), nitro (or halo or lower alkoxy)phenyl(lower)alkoxycarbonyl (e.g. nitrobenzyloxycarbonyl, chlorobenzyloxycarbonyl, methoxybenzyloxycarbonyl, etc.), lower alkoxyaroyl such as lower alkoxybenzoyl (e.g. anisoyl, ethoxybenzoyl, etc.), and the like.

Suitable "di(lower)alkylaminomethylene" may include dimethylaminomethylene, diethylaminomethylene, dipropylaminomethylene, and the like.

The preferred embodiments of "mono- or di-substituted amino" among the above may be mono- or di-(lower)alkylamino, mono, or di-(lower)alkanesulfonamido, mono- or di-(lower)alkanamido, mono- or di-(lower)-alkoxalylamino, mono- or di-aroylamino optionally substituted by lower alkoxy, mono- or di-($C_3$-$C_7$)cycloalkanamido, N'-(lower)alkylureido, N-

(lower)alkyl(lower)alkanamido, [N,N-di(lower)al-kylamino]methyleneamino, and the like.

Suitable "halogen" for $R^2$ may include fluorine, chlorine, bromine and iodine, in which the most preferred one is chlorine.

Suitable "lower alkyl" for $R^2$ may include the same ones as those exemplified for "lower alkyl" as the substituent in $R^1$.

Suitable "acyl" for $R^2$ may include phenyl, tolyl, xylyl, cumenyl, mesityl, naphthyl and the like, in which the most preferred one is phenyl.

Suitable "ar(lower)alkyl optionally substituted by halogen" for $R^3$ may include mono(or di or tri)phenyl(-lower)alkyl (e.g. benzyl, phenethyl, benzhydryl, trityl, etc.), mono(or di tri)phenyl(lower)alkyl substituted by 1 to 5 halogen atom(s) as exemplified for $R^2$ (e.g. chlorobenzyl, bromobenzyl, fluorobenzyl, chlorophenethyl, dichlorobenzyl, trichlorobenzyl, tetrachlorobenzyl, pentachlorobenzyl, chlorobenzhydryl, etc.), and the like, in which the preferred one is diphenyl(lower)alkyl optionally substituted by 1 to 5 halogen atom(s).

Suitable "lower alkylene optionally interrupted by a sulfur atom" for A may include lower alkylene (e.g. methylene, ethylene, propylene, trimethylene, tetramethylene, pentamethylene, etc.), lower alkylene interrupted by a sulfur atom of the formula: $-A^1-S-A^2-$, in which $A^1$ and $A^2$ are each lower alkylene as exemplified above.

Suitable "$C_1$-$C_3$alkylene" for Y may include methylene, ethylene, propylene, trimethylene and the like, and the most preferred one is ethylene.

Suitable pharmaceutically acceptable salts of the object compounds (I) are conventional non-toxic salts and may include an acid addition salt such as an inorganic acid addition salt (e.g. hydrochloride, hydrobromide, sulfate, phosphate, etc.), an organic acid addition salt (e.g. oxalate, maleate, lactate, tartrate, fumarate, methanesulfonate, benzenesulfonate, toluenesulfonate, etc.) or a salt with an amino acid (e.g. aspartic acid, glutamic acid, etc.), a salt with a base such as alkali metal salt (e.g. sodium salt, potassium salt, etc.), and the like.

The object compounds (I) of the present invention can be prepared by the following processes.

Process 1:

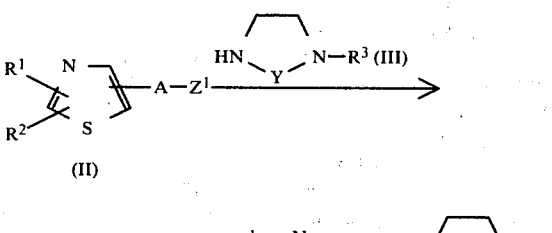

(I)

Process 2:

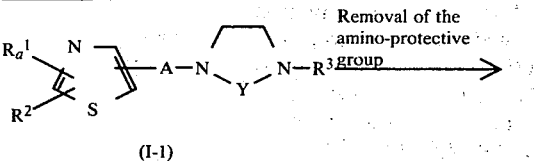

Process 3:

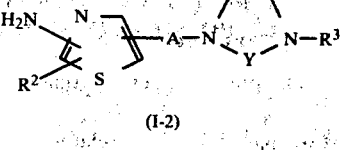

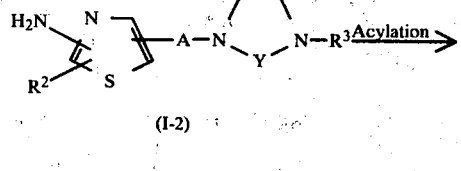

Process 4:

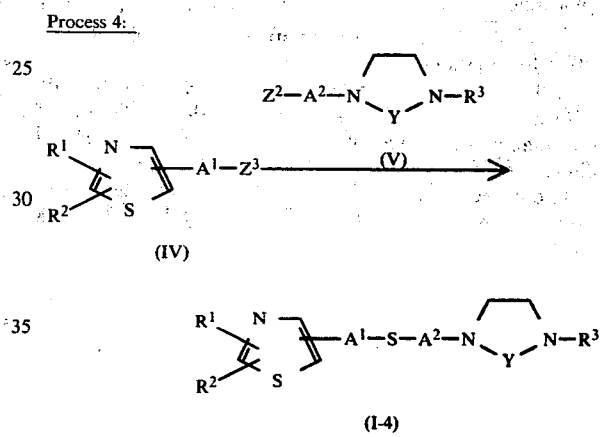

wherein
$R^1$, $R^2$, $R^3$, A, $A^1$, $A^2$ and Y are each as defined above,
$R_a^1$ is a protected amino group,
$R_b^1$ is an acylamino group,
$Z^1$ is an acid residue, and
one of $Z^2$ and $Z^3$ is mercapto and the other is an acid residue.

Suitable protective group in the "protected amino" for $R_a^1$ may include an acyl group as exemplified for the acyl group as a substituent in $R^1$.

Suitable acyl moiety in the "acylamino" for $R_b^1$ may include the same ones as the above.

Suitable "acid residue" for $Z^1$, $Z^2$ and $Z^3$ may include halogen (e.g. chlorine, bromine, iodine, etc.), azido, acyloxy (e.g. benzenesulfonyloxy, tosyloxy, etc.) and the like.

The aforementioned processes for preparing the object compounds (I) of the present invention are explained in detail in the following.

Process 1:

The compound (I) or its salt can be prepared by reacting a compound (II) or its salt with a compound (III) or its salt.

Suitable salt of the compounds (II) and (III) may be ones as exemplified before.

This reaction can preferably be carried out in the presence of an organic or inorganic base such as tri(- lower)alkylamine (e.g. trimethylamine, triethylamine, etc.), N,N-di(lower)alkyl arylamine (e.g. N,N-dimethylaniline, etc.), N,N-di(lower)alkyl ar(lower)alkylamine (e.g. N,N-dimethyl benzylamine, etc.), pyridine, picoline, 1,5-diazabicyclo[4,3,0]non-5-ene, 1,4-diazabicyclo[2,2,2]octane, 1,5-diazabicyclo[5,4,0]undecene-5, alkali metal acetate (e.g. sodium acetate, potassium acetate, etc.), alkali metal lower alkoxide (e.g. sodium methoxide, sodium ethoxide, potassium tert-butoxide, etc.), alkali metal hydride (e.g. sodium hydride, potassium hydride, etc.), alkali metal hydroxide (e.g. sodium hydroxide, potassium hydroxide, etc.), alkaline earth metal hydroxide (e.g. magnesium hydroxide, calcium hydroxide, etc.), alkali metal carbonate (e.g. sodium carbonate, potassium carbonate, etc.), alkaline earth metal carbonate (e.g. magnesium carbonate, calcium carbonate, etc.), alkali metal bicarbonate (e.g. sodium bicarbonate potassium bicarbonate, etc.), or the like.

This reaction can also be carried out in the presence of a reaction stimulator such as metal halide (e.g. sodium iodide, potassium iodide, etc.) or the like.

This reaction is usually carried out in a conventional solvent such as methanol, benzene, acetone, dioxane, N,N-dimethylformamide or any other solvent which does not adversely influence the reaction.

The reaction temperature is not critical, and the reaction is usually carried out under warming or heating.

Process 2:

The compound (I-2) or its salt can be prepared by subjecting a compound (I-1) to removing reaction of the amino-protective group in $R_a^1$.

Suitable method for this reaction may include hydrolysis, hydrogenolysis, and the like.

In case that the reaction is conducted by hydrolysis, it is preferably carried out in the presence of an acid or a base.

Suitable acid may include an inorganic acid (e.g. hydrochloric acid, hydrobromic acid, sulfuric acid, etc.), an organic acid (e.g. formic acid, acetic acid, trifluoroacetic acid, propionic acid, benzenesulfonic acid, p-toluenesulfonic acid, etc.), and the like.

Suitable base may include ones as exemplified in the explanation of Process 1.

The hydrolysis is usually carried out in a conventional solvent such as water, methanol, ethanol, tetrahydrofuran, dioxane, N,N-dimethylformamide or any other solvent which does not adversely influence the reaction.

The reaction temperature is not critical, and the reaction is usually carried out at ambient temperature or under warming or heating.

In case that the removing reaction is conducted by hydrogenolysis, it is carried out by conventional catalytic reduction, and suitable catalyst may be palladium catalyst (e.g. palladium on charcoal, palladium on barium sulfate, colloidal palladium, spongy palladium, etc.), platinum catalyst (e.g. platinum plate, platinum wire, platinum black, spongy platinum etc.), and the like.

The catalytic reduction is usually carried out in a conventional solvent such as water, methanol, ethanol, propanol or any other solvent which does not adversely influence the reaction.

The reaction temperature is not critical, and the reaction is usually carried out at ambient temperature or under warming.

Process 3:

The compound (I-3) or its salt can be prepared by reacting a compound (I-2) or its salt with an acylating agent.

Suitable acylating agent may include an acid and its reactive derivative containing the acyl group as exemplified before.

Suitable example of the reactive derivative may be acid halide (e.g. acid chloride, acid bromide, etc.), acid anhydride such as acid anhydride with lower alkanoic acid (e.g. acetic acid, etc.) or mono(lower)alkyl carbonate (e.g. monoethyl carbonate, etc.), activated amide (e.g. amide with pyrazole, imidazole, 4-methylimidazole, etc.), activated ester (e.g. cyanomethyl ester, methoxymethyl ester, p-nitrophenyl ester, etc.), and the like.

The reaction can be carried out in the presence of an organic or inorganic base as exemplified in the explanation of Process 1.

In case that the acylating agent is used in a form of free acid, the reaction can preferably be carried out in the presence of a condensing agent such as a carbodiimide compound (e.g., N,N'-dicyclohexylcarbodiimide, N-cyclohexyl-N'-morpholinoethylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, etc.), a ketenimine compound (e.g., N,N'-carbonylbis(2-methylimidazole), pentamethyleneketene-N-cyclohexylimine, diphenylketene-N-cyclohexylimine, etc.); an olefinic or acetylenic ether compound (e.g., ethoxyacetylene β-chlorovinylethyl ether), a sulfonic acid ester of N-hydroxybenzotriazole derivative (e.g., 1-(4-chlorobenzenesulfonyloxy)-6-chloro-1H-benzotriazole, etc.), a phosphorus compound (e.g., trialkyl phosphite, ethyl polyphosphate, isopropyl polyphosphate, phosphoryl chloride, phosphorus trichloride, triphenylphosphine, etc.), thionyl chloride, oxalyl chloride, N-ethylbenzisoxazolium salt, N-ethyl-5-phenylisoxazolium-3'-sulfonate, a reagent (referred to as so-called "Vilsmeier reagent") formed by the reaction of an amide compound (e.g. dimethylformamide, diethylformamide, etc.) with a halogen compound (e.g. thionyl chloride, phosphoryl chloride, phosgene, etc.), and the like.

This reaction is usually carried out in a conventional solvent such as methylene chloride, chloroform, ethylene chloride, acetone, methanol, ethanol, tetrahydrofuran, pyridine, N,N-dimethylformamide or any other solvent which does not adversely influence the reaction.

The reaction temperature is not critical, and the reaction is usually carried out under cooling or at ambient temperature.

Process 4:

The compound (I-4) or its salt can be prepared by reacting a compound (IV) or its salt with a compound (V) or its salt.

Suitable salt of the compound (IV) may be ones as exemplified before and that of the compound (V) may be an acid addition salt as exemplified before.

This reaction can be carried out in substantially the same manner as that of Process 1, and therefore, the reaction mode and reaction conditions (e.g. solvent, reaction temperature, etc.) can be referred to the explanation of Process 1.

The object compounds (I) obtained in the above Processes 1 to 4 can be isolated and purified in a conventional manner, for example, extraction, precipitation, fractional chromatography, fractional crystallization, recrystallization, and the like.

The object compounds (I) thus prepared can be transformed into optional pharmaceutically acceptable salt by a conventional method, if desired.

Some of the starting compound (II) are novel and can be prepared by the following processes, and the others can be prepared by a similar method thereto or a conventional manner.

Process A:

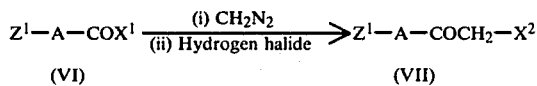

Process B:

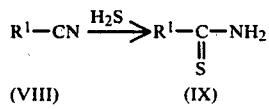

Process C:

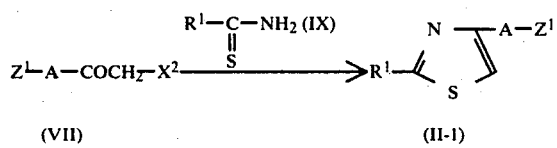

Process D:

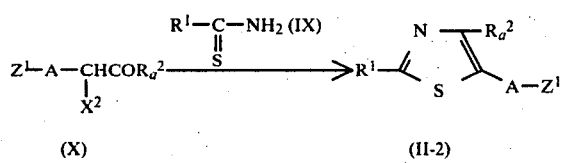

Process E:

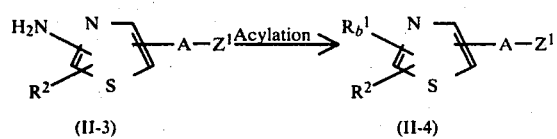

Process F:

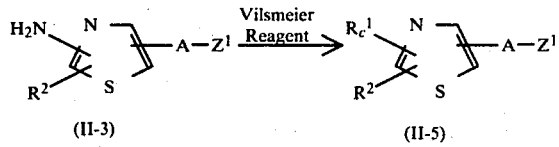

wherein
$R^1$, $R_b^1$, $R^2$, A and $Z^1$ are each as defined above,
$R_c^1$ is [N,N-di(lower)alkylaminomethylene]amino,
$R_a^2$ is lower alkyl, and
$X^1$ and $X^2$ are each halogen.

Suitable "[N,N-di(lower)alkylaminomethylene]amino" for $R_c^1$, "lower alkyl" for $R_a^2$ and "halogen" for $X^1$ and $X^2$ may be the same ones as those exemplified before, respectively.

The processes for preparing the starting compounds are explained in more detail in the following.

Process A:

The compound (VII) can be prepared by reacting a compound (VI) with diazomethane and then with hydrogen halide.

Suitable "hydrogen halide" may include hydrogen chloride, hydrogen bromide, and the like.

The reaction is usually carried out in a solvent such as diethyl ether or any other solvent which does not adversely influence the reaction.

The reaction temperature is not critical, and the reaction is usually carried out under cooling or at ambient temperature.

Process B:

The compound (IX) can be prepared by reacting a compound (VIII) with hydrogen sulfide.

The reaction is preferably carried out in the presence of a base as exemplified in the explanation of Process 1.

The reaction is usually carried out in a solvent such as pyridine or any other solvent which does not adversely influence the reaction.

The reaction temperature is not critical, and the reaction is usually carried out at ambient temperature or under warming or heating.

Process C:

The compound (II-1) or its salt can be prepared by reacting a compound (VII) with a compound (IX).

The reaction is usually carried out in a solvent such as water, methanol, ethanol, propanol or any other solvent which does not adversely influence the reaction.

The reaction temperature is not critical, and the reaction is usually carried out under warming or heating.

Process D:

The compound (II-2) or its salt can be prepared by reacting a compound (X) with a compound (IX).

This reaction can be carried out in substantially the same manner as that of Process C, and therefore, the reaction mode and reaction conditions (e.g. solvent, reaction temperature, etc.) can be referred to the explanation of Process C.

Process E:

The compound (II-4) or its salt can be prepared by reacting a compound (II-3) or its salt with an acylating agent.

Suitable acylating agent may be the same as those exemplified in the explanation of Process 3.

This reaction can be carried out in substantially the same manner as that of Process 3, and therefore, the reaction mode and reaction conditions (e.g. solvent, reaction temperature, etc.) can be referred to the explanation of Process 3.

Process F:

The compound (II-5) can be prepared by reacting a compound (II-3) or its salt with Vilsmeier Reagent.

Vilsmeier Reagent used in this process can be prepared in a conventional manner, for example, by reacting N,N-di(lower)alkylformamide with a halogenating agent such as phosphorus oxychloride, phosphorus trihalide (e.g. phosphorus tribromide, phosphorus trichloride, etc.), phosphorus pentahalide (e.g. phosphorus pentachloride, etc.), lower alkanesulfonyl halide (e.g. methanesulfonyl chloride, ethanesulfonyl chloride, etc.) or the like.

The reaction is usually carried out in the presence of pyridine.

The reaction temperature is not critical, and the reaction is usually carried out at a temperature range from cooling to heating.

The object compounds (I) and pharmaceutically acceptable salts thereof obtained according to the processes of this invention have potent and long lasting antiallergic activity and can be used therapeutically as well as prophylactically as antiallergic agents for relieving or inhibiting allergic symptoms of human being and animals.

Test Compound

Compound A: 4-(4-Benzhydrylpiperazin-1-ylmethyl)-2-methanesulfonamidothiazole

Compound B: 4-(4-Benzhydrylpiperazin-1-ylmethyl)-2-ethanesulfonamidothiazole

Compound C: 4-(4-Benzhydrylpiperazin-1-ylmethyl)-2-propanesulfonamidothiazole

Compound D: 4-[3-(4-Benzhydrylpiperazin-1-yl)-propyl]-2-acetamidothiazole

Test Method (1) Preparation of rabbit antiserum against egg albumin

Equal volumes of a saline solution of egg albumin (200 mg/ml) and of Freund's Complete Ajuvant were mixed and emulsified. Each male New Zealand white strain rabbits, each weighing 2 to 2.5 kg., received an intramuscular injection of 0.5 ml of the emulsion in the left and right thigh regions. One week later, they received an intradermal injection of 0.25 ml of a saline solution of egg albumin (concentration: 20 mg/ml) in the different four sites of the dorsal skin surface three times every other week. Blood samples were collected from the carotid artery one week after the last injection.

(2) Determination of Passive Cutaneous Anaphylaxis (PCA) Titer

The level of anaphylactic anti-egg albumin antibodies in pools of sera were determined by passive cutaneous anaphylaxis (PCA) reactions using shaven Hartley strain test guinea-pigs.

Antiserum was serially diluted (two fold) in saline and 0.1 ml of each antiserum dilution were injected intradermally into the dorsal skin surface of the test guinea-pigs. 24 hours after intradermal sensitization, Egg albumin-specific PCA reactions were elicited by intravenous injection of 10 mg of egg albumin in 1 ml of 1% Evans blue dye dissolved in saline. Reactions were read and recorded as the highest dilution of serum evoking threshold PCA reactivity (5 mm diameter).

(3) Antagonism to anaphylactic asthma in guinea-pigs

Male Hartley strain guinea-pigs, weighing 305 to 400 g, were used. Animals were sensitized by an intravenous injection of rabbit antiserum against egg albumin (4000 PCA titer) with 0.5 ml/animal. After 24 hours, animals were placed individually in a plastic chamber of 5.3 liter volume. An aerosol of 5% egg albumin solution was sprayed in the chamber at a rate of 0.16 ml/min with a commercial nebulizer. The test compounds were given to the animals orally 30 minutes before the challenge with the egg albumin solution. Each dose group consisted of 3 or 5 animals. The inhibitory effect of the test compounds was determined from the number of surviving animals more than 2 hours after spray of the antigen.

Test Results

Inhibitory effect of anaphylactic asthma in guinea-pig

| Test Compounds | Inhibitory Effect (%) | |
|---|---|---|
| | Dose 10 mg/kg | Dose 1 mg/kg |
| A | 100 | 100 |
| B | 100 | 67 |
| C | 100 | 100 |
| D | 100* | 40* |

*Dose group: 5 guinea-pigs

As being apparent from the above test results, the object compounds (I) of the present invention are useful for the antiallergic medicines.

For therapeutic administration, the object compounds (I) of the present invention and pharmaceutically acceptable salts thereof are used in a form of the conventional pharmaceutical preparation in admixture with a conventional pharmaceutically acceptable carrier such as an organic or inorganic solid or liquid excipient which is suitable for oral, parenteral or external administration.

The pharmaceutical preparation may be compounded in a solid form such as capsule, tablet, dragee, ointment or suppository, or in a liquid form such as solution, suspension or emulsion. If needed, there may be included in the above preparation auxiliary substance, stabilizing agent, wetting or emulsifying agent, buffer or any other commonly used additives.

The effective ingredient may usually be administered with a unit dose of 1 mg/kg to 500 mg/kg., 1 to 4 times a day. However, the above dosage may be increased or decreased according to age, weight and conditions of the patient or the administering method.

The following examples are given only for the purpose of illustrating the present invention in more detail.

Preparation of the starting compounds

Preparation 1

(1) To a suspension of N-methyl-N-nitrosourea (25.0 g) in diethyl ether (130 ml) was added dropwise 40% aqueous solution of potassium hydroxide (52 ml) below 5° C., and the separated organic layer was dried over potassium hydroxide to prepare a solution of diazomethane in diethyl ether. To this solution was added dropwise a solution of 3-chloropropionyl chloride (8.0 g) in diethyl ether (40 ml) below −5° C. over a period of 20 minutes with stirring, and the stirring was continued at the same temperature for 2 hours. After hydrogen chloride was introduced into the reaction mixture for about an hour, nitrogen was additionally introduced thereinto for about half an hour, followed by concentration. After dissolving it in diethyl ether and drying over anhydrous magnesium sulfate, the solution was evaporated to dryness to give an oil, which was purified by distillation to obtain 1,4-dichloro-2-butanone (5.6 g), bp 92.5°–94° C./20 mmHg.

IR cm$^{-1}$ (Film): 1725, 1400, 1298, 1080, 960, 772.

NMR δppm (CCl$_4$): 3.18 (2H, t, J=10.0 Hz), 3.84 (2H, t, J=10.0 Hz), 4.17 (2H, s).

(2) 5.4 g of this product was added to an aqueous solution (52 ml) of thiourea (2.92 g) and heated at 100° C. for half an hour. After concentration under reduced pressure, the residue was neutralized with 1 N aqueous solution of sodium hydroxide, followed by extracting with diethyl ether. The extract was washed with water, dried over anhydrous magnesium sulfate and then evaporated to obtain an oil (5.9 g) of 2-amino-4-(2-chloroethyl)thiazole.

(3) A solution of this compound in acetic anhydride (30 ml) was refluxed under heating for 1.5 hours, followed by concentration. The residue was recrystallized from benzene to obtain white crystals (5.45 g) of 2-acetamido-4-(2-chloroethyl)thiazole, mp 161°–163° C.

IR cm$^{-1}$ (Nujol): 3160, 1633, 1320, 1000, 942, 724.

NMR δppm (DMSO-d$_6$): 2.13 (3H, s), 3.05 (2H, t, J=7.0 Hz), 3.89 (2H, t, J=7.0 Hz), 6.9 (1H, s), 12.85 (1H, s).

Preparation 2

(1) 1,5-Dichloro-2-pentanone (12.9 g) was obtained by reacting 4-chlorobutyryl chloride (16.5 g) with diazomethane in diethyl ether and hydrogen chloride according to a similar manner to that of Preparation 1-(1), bp 72°–95° C./4–8 mmHg.

(2) 2-Amino-4-(3-chloropropyl)thiazole (2.6 g) was obtained by reacting 1,5-dichloro-2-pentanone (3.1 g) with thiourea (1.52 g) according to a similar manner to that of Preparation 1-(2).

(3) 2-Acetamido-4-(3-chloropropyl)thiazole (2.4 g) was obtained by reacting 2-amino-4-(3-chloropropyl)thiazole (2.5 g) with acetyl chloride (1.1 ml) according to a similar manner to that of Preparation 1-(3), mp 110°–112° C.

IR cm$^{-1}$ (Nujol): 3200, 1645, 1555, 1300, 1000.

NMR δppm (DMSO-d$_6$): 2.20 (2H, m), 2.25 (3H, s), 2.86 (2H, t, J=7.0 Hz), 3.55 (2H, t, J=7.0 Hz), 6.58 (1H, s), 9.0 (1H, s).

Preparation 3

(1) 2-Amino-5-(2-chloroethyl)-4-methylthiazole monohydrobromide (5.1 g) was obtained by reacting 3-bromo-5-chloro-2-pentanone (6.0 g) with thiourea (2.3 g) according to a similar manner to that of Preparation 1-(2).

(2) 2-Acetamido-5-(2-chloroethyl)-4-methylthiazole (1.85 g) was obtained by reacting 2-amino-5-(2-chloroethyl)-4-methylthiazole monohydrobromide (2.8 g) with acetic anhydride (30 ml) according to a similar manner to that of Preparation 1-(3), mp 172°–174° C.

IR cm$^{-1}$ (Nujol): 3140, 1685, 1275, 718.

NMR δppm (DMSO-d$_6$): 2.05 (3H, s), 2.15 (3H, s), 3.20 (2H, t, J=8.0 Hz), 3.75 (2H, t, J=8.0 Hz).

Preparation 4

4-Chloromethyl-2-isopropylthiazole (5.5 g) was obtained by reacting thioisobutyramide (3.09 g) with 1,3-dichloro-2-propanone (3.81 g) in ethanol (50 ml) according to a similar manner to that of Preparation 1-(2).

IR (Film): 2960, 2925, 2860, 1610, 1480, 1460, 1265, 1155, 1060, 875, 730 cm$^{-1}$.

Preparation 5

4-Chloromethyl-2-(N-methylacetamido)thiazole (3.1 g) was obtained by reacting 4-chloromethyl-2-(N-methylamino)thiazole monohydrochloride (5.6 g) with acetic anhydride (30 ml) according to a similar manner to that of Preparation 1-(3), mp 138°–140° C.

IR cm$^{-1}$ (Nujol): 1660, 1480, 1005, 715, 705.

NMR δppm (DMSO-d$_6$): 2.35 (3H, s), 3.78 (3H, s), 4.80 (2H, s), 7.30 (1H, s).

PREPARATION OF THE OBJECT COMPOUNDS

Example 1

A mixture of 2-acetamido-4-chloromethylthiazole (7.6 g), 1-benzhydrylpiperazine (10.0 g) and potassium carbonate (5.5 g) in N,N-dimethylformamide (80 ml) was stirred at 80° C. for 2 hours. After the reaction mixture was poured into ice-water, the precipitated crystals were collected by filtration, washed with water and then crystallized twice from methanol to give white crystals (8.4 g) of 2-acetamido-4-(4-benzhydrylpiperazin-1-ylmethyl)thiazole, mp 178°–179° C.

IR cm$^{-1}$ (Nujol): 3300, 3200, 1690, 1575, 1450, 1290, 705.

NMR δppm (DMSO-d$_6$): 2.10 (3H, s), 2.41 (8H, m), 3.52 (2H, s), 4.19 (1H, s), 6.93 (1H, s), 7.40 (10H, m), 10.40 (1H, s).

| Elemental Analysis: C$_{23}$H$_{26}$N$_4$OS | | |
|---|---|---|
| C | H | N |
| Calcd. 67.95 | 6.44 | 13.78 |
| Found 68.21 | 6.63 | 13.59 |

Example 2

2-Acetamido-4-[4-(4-chlorobenzhydryl)piperazin-1-ylmethyl]thiazole (5.4 g) was obtained by reacting 2-acetamido-4-chloromethylthiazole (3.8 g) with 1-(4-chlorobenzhydryl)piperazine (5.7 g) according to a similar manner to that of Example 1, mp 140°–145° C.

IR cm$^{-1}$ (Nujol): 3300, 1695, 1545, 1000, 760.

NMR δppm (DMSO-d$_6$): 2.01 (3H, s), 2.3–2.5 (8H, m), 3.45 (2H, s), 4.22 (1H, s), 6.85 (1H, s), 7.05–7.30 (9H, m), 11.5 (1H, s).

| Elemental Analysis: C$_{23}$H$_{25}$ClN$_4$OS | | |
|---|---|---|
| C | H | N |
| Calcd. 62.50 | 5.70 | 12.67 |
| Found 62.01 | 5.61 | 12.53 |

Example 3

A mixture of 2-acetamido-4-chloromethylthiazole (0.95 g), 1-benzhydrylperhydro-1,4-diazepine (1.33 g) and potassium carbonate (0.7 g) in N,N-dimethylformamide (5 ml) was stirred at 70° C. for an hour. After the reaction mixture was poured into ice-water, it was extracted with ethyl acetate. The extract was washed with water, dried over anhydrous magnesium sulfate and then evaporated to give an amorphous product (1.7 g), which was chromatographed on silica gel (30 g) using a mixture of chloroform and methanol (20:1 by volume) as an eluent. The eluates containing the desired compound were collected and then evaporated to give an oil (1.4 g), which was dissolved in a mixture of methanol (10 ml) and conc. hydrochloric acid (5 ml), followed by refluxing for an hour. After removal of the methanol, the remained aqueous solution was neutralized with an aqueous solution of sodium bicarbonate. The precipitated crystals were collected by filtration, washed with water and then dried, followed by recrystallization from ethyl acetate to obtain pale yellow crystals (0.75 g) of 2-amino-4-(4-benzhydryl-perhydro-1,4-diazepin-1-ylmethyl)thiazole, mp 152°–156° C.

IR cm$^{-1}$ (Nujol): 3230, 1650, 1590, 1530, 710, 700.

NMR δppm (DMSO-d$_6$): 1.62 (2H, m), 2.3-2.5 (8H, m), 3.35 (2H, s), 4.64 (1H, s), 6.15 (1H, s), 6.75 (2H, s), 7.0-7.45 (10H, m).

| Elemental Analysis: C$_{22}$H$_{26}$N$_4$S | | | |
|---|---|---|---|
| | C | H | N |
| Calcd. | 69.80 | 6.92 | 14.80 |
| Found | 70.01 | 6.94 | 14.65 |

Example 4

A mixture of 2-acetamido-4-(2-chloroethyl)thiazole (4.56 g), 1-benzhydrylpiperazine (5.62 g) and potassium carbonate ( 3.08 g) in N,N-dimethylformamide (45 ml) was stirred at 65° C. for 3.5 hours and at 100° C. for additional 10 hours. After concentration of the reaction mixture, thereto was added ice-water, followed by extraction with ethyl acetate. The extract was washed with water, dried over anhydrous magnesium sulfate and then evaporated to give an amorphous product (10 g), which was chromatographed on silica gel (300 g) using a mixture of chloroform and methanol (20:1 by volume) as an eluent. The eluates containing the desired compound were collected and then evaporated to give an amorphous product, which was transformed into its hydrochloride in a conventional manner, followed by recrystallization from a mixture of methanol and diethyl ether to obtain 2-acetamido-4-[2-(4-benzhydrylpiperazin-1-yl)ethyl]thiazole trihydrochloride (4.95 g), mp 182°-190° C.

IR cm$^{-1}$ (Nujol): 1660, 1550, 1290, 1005.

NMR δppm (DMSO-d$_6$): 2.24 (3H, s), 3.0-4.2 (12H, m), 6.1 (1H, broad), 7.06 (1H, s), 7.53 (5H, m), 8.10 (5H, m).

| Elemental Analysis: C$_{24}$H$_{28}$N$_4$OS.3HCl.5/4H$_2$O | | | | |
|---|---|---|---|---|
| | C | H | N | H$_2$O |
| Calcd. | 51.38 | 5.77 | 9.98 | 4.07 |
| Found | 51.69 | 5.94 | 9.83 | 4.04 |

Example 5

2-Acetamido-4-[2-{4-(4-chlorobenzhydryl)piperazin-1-yl}ethyl]thiazole dihydrochloride (4.5 g) was obtained by reacting 2-acetamido-4-(2-chloroethyl)thiazole (6.0 g) with 1-(4-chlorobenzhydryl)piperazine (8.6 g) according to a similar manner to that of Example 4, mp 160°-190° C.

IR cm$^{-1}$ (Nujol): 3400, 2700-2350, 1695, 1550, 710.

NMR δppm (DMSO-d$_6$): 2.05 (3H, s), 3.1-3.7 (10H, broad), 5.55 (1H, broad), 6.90 (1H, s), 7.35-7.80 (9H, m).

Example 6

A mixture of 2-acetamido-4-(3-chloropropyl)thiazole (35.2 g), 1-benzhydrylpiperazine (40.8 g), potassium carbonate (22.3 g) and potassium iodide (1.0 g) in N,N-dimethylformamide (280 ml) was stirred at 70° C. for 3 hours. After concentration of the reaction mixture, it was extracted with ethyl acetate, followed by removal of the insoluble substance by filtration. The filtrate was washed with water, dried over anhydrous magnesium sulfate and then evaporated to give an oil (55 g), which was chromatographed on silica gel (700 g) using a mixture of chloroform and methanol (100:1 by volume) as an eluent. The eluates containing the desired compound were collected and then evaporated to give an amorphous product (15.5 g), which was transformed into its fumarate in a conventional manner, followed by recrystallization from ethanol to obtain white crystals (11.2 g) of 2-acetamido-4-[3-(4-benzhydrylpiperazin-1-yl)propyl]thiazole hemifumarate, mp 213°-215° C.

IR cm$^{-1}$ (Nujol): 3150, 3100, 1690, 1540, 750, 710.

NMR δppm (DMSO-d$_6$): 1.80 (2H, m), 2.09 (3H, s), 2.2-2.6 (12H, broad), 4.26 (1H, s), 6.05 (2H, broad), 6.53 (1H, s), 6.66 (1H, s), 7.05-7.55 (10H, m).

| Elemental Analysis: C$_{25}$H$_{30}$N$_4$OS.½C$_4$H$_4$O$_4$ | | | |
|---|---|---|---|
| | C | H | N |
| Calcd. | 65.83 | 6.53 | 11.37 |
| Found | 65.75 | 6.61 | 11.19 |

Example 7

A mixture of 4-chloromethyl-2-methylthiazole hydrochloride (1.84 g), 1-benzhydrylpiperazine (2.52 g) and potassium carbonate (2.7 g) in N,N-dimethylformamide (15 ml) was stirred at 70° C. for an hour. After the reaction mixture was poured into ice-water, it was extracted with ethyl acetate. The extract was washed with water, dried over anhydrous magnesium sulfate and then evaporated to give a residue, which was transformed into its hydrochloride in a conventional manner, followed by recrystallization from a mixture of methanol and diethyl ether to obtain white crystals (2.0 g) of 4-(4-benzhydrylpiperazin-1-ylmethyl)-2-methylthiazole trihydrochloride, mp 166°-170° C. (dec.).

IR cm$^{-1}$ (Nujol): 2800-2400, 1600, 1500, 705.

NMR δppm (DMSO-d$_6$): 2.78 (3H, s), 3.6-3.8 (8H, broad), 4.62 (2H, s), 6.15 (1H, s), 7.50 (7H, m), 8.05 (7H, m).

| Elemental Analysis: C$_{22}$H$_{25}$N$_3$S.3HCl.½H$_2$O | | | | |
|---|---|---|---|---|
| | C | H | N | H$_2$O |
| Calcd. | 54.82 | 6.01 | 8.70 | 1.86 |
| Found | 54.59 | 6.21 | 8.45 | 1.69 |

Example 8

4-[4-(4-Chlorobenzhydryl)piperazin-1-ylmethyl]-2-methylthiazole monofumarate (2.6 g) was obtained by reacting 4-chloromethyl-2-methylthiazole monohydrochloride (1.84 g) with 1-(4-chlorobenzhydryl)piperazine (2.86 g) according to a similar manner to that of Example 7, mp 195°-197° C.

IR cm$^{-1}$ (Nujol): 2600, 1710, 1635, 1580, 1200, 760.

NMR δppm (DMSO-d$_6$): 2.4-2.55 (8H, m), 2.65 (3H, s), 3.75 (2H, s), 4.25 (1H, s), 6.65 (2H, s), 7.2-7.5 (10H, m), 9.91 (2H, broad).

| Elemental Analysis: C$_{22}$H$_{24}$ClN$_3$S.C$_4$H$_4$O$_4$ | | | |
|---|---|---|---|
| | C | H | N |
| Calcd. | 60.75 | 5.49 | 8.17 |
| Found | 60.74 | 5.44 | 8.02 |

Example 9

A mixture of 4-chloromethyl-2-methylaminothiazole monohydrochloride (2.2 g), 1-benzhydrylpiperazine (2.5 g) and potassium carbonate (2.7 g) in N,N-dimethylformamide (15 ml) was stirred at 70° C. for an hour. After the reaction mixture was poured into ice-water, it was extracted with ethyl acetate. The extract was washed with water, dried over anhydrous magnesium sulfate and then evaporated to dryness to give an oil, which was transformed into its hydrochloride in a conventional manner, followed by recrystallization from a mixture of methanol and diethyl ether to obtain white crystals (1.2 g) of 4-(4-benzhydrylpiperazin-1-ylmethyl)-2-methylaminothiazole trihydrochloride, mp 225°–228° C. (dec.).

IR cm$^{-1}$ (Nujol): 3450, 3170, 2800–2400, 1625, 1500, 710.

NMR δppm (DMSO-d$_6$): 3.00 (3H, s), 3.4–3.7 (8H, broad), 4.35 (2H, s), 5.75 (1H, s), 7.20 (1H, s), 7.45–7.8 (10H, m), 8.6 (5H, broad).

Example 10

A mixture of 4-chloromethyl-2-(N-methylacetamido)thiazole (2.05 g), 1-benzhydrylpiperazine (2.5 g) and potassium carbonate (1.4 g) in N,N-dimethylformamide (20 ml) was stirred at 80° C. for 1.5 hours. After the reaction mixture was poured into ice-water, the precipitated crystals were washed with water and then dried, followed by recrystallization from a mixture of ethyl acetate and n-hexane to obtain pale yellow crystals of 4-(4-benzhydrylpiperazin-1-ylmethyl)-2-(N-methylacetamido)thiazole (1.3 g), mp 140°–142° C.

IR cm$^{-1}$ (Nujol): 1655, 1490, 1000, 760, 705.

NMR δppm (DMSO-d$_6$): 2.25 (3H, s), 2.3–2.55 (8H, m), 3.52 (2H, s), 3.60 (3H, s), 4.25 (1H, s), 6.90 (1H, s), 7.1–7.5 (10H, m).

| Elemental Analysis: C$_{24}$H$_{28}$N$_4$OS | | | |
|---|---|---|---|
| | C | H | N |
| Calcd. | 68.54 | 6.71 | 13.32 |
| Found | 68.49 | 6.58 | 13.25 |

Example 11

(1) A solution of 1-bromo-5-chloro-2-pentanone (6.7 g) and thioacetamide (2.5 g) in methanol (10 ml) was stirred at 50° C. for 5 hours. After concentration of the reaction mixture, the residue was allowed to stand for 10 days. The crystalline residue was suspended in a mixture of methanol and diethyl ether and the remained solid was collected by filtration to give brown powder (7.3 g) of 4-(3-chloropropyl)-2-methylthiazole monohydrobromide.

(2) A mixture of the above object compound (2.6 g), 1-benzhydrylpiperazine (2.5 g) and potassium carbonate (2.75 g) in N,N-dimethylformamide (20 ml) was stirred at 70° C. for 2 hours. After concentration of the reaction mixture, the concentrate was extracted with ethyl acetate. The extract was washed with water, dried over anhydrous magnesium sulfate and then evaporated to give an oily residue (4.4 g), which was chromatographed on silica gel (80 g) using a mixture of ethyl acetate and methanol (50:1 by volume) as an eluent. The eluates containing the desired compound were collected and evaporated to dryness under reduced pressure to give an oil (1.25 g), which was transformed into its fumarate in a conventional manner, followed by recrystallization from a mixture of ethanol and diethyl ether to obtain white crystals (0.5 g) of 4-[3-(4-benzhydrylpiperazin-1-yl)propyl]-2-methylthiazole monofumarate, mp 183°–185° C.

IR cm$^{-1}$ (Nujol): 2500–2300, 1690, 1635, 1580, 1200, 760, 710.

NMR δppm (DMSO-d$_6$): 1.86 (2H, m), 2.45–2.85 (15H, m), 4.31 (1H, s), 6.61 (2H, s), 7.08 (1H, s), 7.15–7.55 (10H, m), 8.2 (2H, broad).

| Elemental Analysis: C$_{24}$H$_{29}$N$_3$S·C$_4$H$_4$O$_4$ | | | |
|---|---|---|---|
| | C | H | N |
| Calcd. | 66.25 | 6.55 | 8.28 |
| Found | 66.11 | 6.54 | 8.19 |

Example 12

A mixture of 4-chloromethylthiazole monohydrochloride (1.7 g), 1-benzhydrylpiperazine (3.21 g) and potassium carbonate (5.3 g) in N,N-dimethylformamide (40 ml) was stirred at 65° C. for 2 hours. After concentration of the reaction mixture, the concentrate was extracted with ethyl acetate. The extract was washed with water, dried over anhydrous magnesium sulfate and then evaporated to dryness to give a residue, which was chromatographed on silica gel (120 g) using a mixture of chloroform and methanol (50:1 by volume) as an eluent. The eluates containing the desired compound were collected and evaporated to dryness under reduced pressure to give crystals, which were recrystallized from chloroform to obtain white crystals (1.2 g) of 4-(4-benzhydrylpiperazin-1-ylmethyl)thiazole, mp 114°–116° C.

IR cm$^{-1}$ (Nujol): 1450, 1310, 1155, 1010, 850, 710.

NMR δppm (DMSO-d$_6$): 2.5 (8H, m), 3.70 (2H, s), 4.20 (1H, s), 7.05–7.50 (11H, m), 8.60 (1H, d, J=3.0 Hz).

| Elemental Analysis: C$_{21}$H$_{23}$N$_3$S | | | |
|---|---|---|---|
| | C | H | N |
| Calcd. | 72.17 | 6.63 | 12.02 |
| Found | 72.08 | 6.61 | 11.85 |

Example 13

A mixture of 2-acetamido-5-(2-chloroethyl)-4-methylthiazole (1.8 g), 1-benzhydrylpiperazine (2.07 g) and potassium carbonate (1.13 g) in N,N-dimethylformamide (20 ml) was stirred at 80° C. for 2.5 hours. After the reaction mixture was poured into ice-water, it was extracted with ethyl acetate. The extract was washed with water, dried over anhydrous magnesium sulfate and then evaporated to give an amorphous product (3 g), which was chromatographed on silica gel (30 g) using ethyl acetate as an eluent. The eluates containing the desired compound were collected and evaporated to dryness to give crystals (1.4 g), which were recrystallized from a mixture of ethyl acetate and diethyl ether to obtain white crystals (0.6 g) of 2-acetamido-5-[2-(4-benzhydrylpiperazin-1-yl)ethyl]-4-methylthiazole, mp 166°–168° C.

IR cm$^{-1}$ (Nujol): 3180, 1695, 1560, 715.

NMR δppm (DMSO-d$_6$): 2.06 (3H, s), 2.11 (3H, s), 2.20–2.80 (12H, m), 4.24 (1H, s), 7.2–7.6 (10H, m), 13.18 (1H, s).

| Elemental Analysis: C$_{25}$H$_{30}$N$_4$OS | | | |
|---|---|---|---|
| | C | H | N |
| Calcd. | 69.09 | 6.96 | 12.89 |

-continued

| Elemental Analysis: $C_{25}H_{30}N_4OS$ | | | |
|---|---|---|---|
| | C | H | N |
| Found | 68.88 | 6.98 | 12.74 |

Example 14

A mixture of 2-acetamido-5-chloro-4-chloromethyl-thiazole (450 mg), 1-benzhydrylpiperazine (504 mg) and potassium carbonate (276 mg) in N,N-dimethylformamide (3 ml) was stirred at 70° C. for 20 minutes. After the reaction mixture was poured into ice-water, the precipitated crystals were collected by filtration, washed with water and then dried, followed by recrystallization from a mixture of ethyl acetate and n-hexane to obtain crystals (355 mg) of 2-acetamido-5-chloro-4-(4-benzhydrylpiperazin-1-ylmethyl)thiazole, mp 227°–230° C.

IR $cm^{-1}$ (Nujol): 3200, 1655, 1550, 760, 705.

NMR δppm (DMSO-$d_6$): 2.10 (3H, s), 2.30 (8H, m), 3.55 (2H, s), 4.21 (1H, s), 7.4–7.6 (10H, m), 14.10 (1H, s).

| Elemental Analysis: $C_{23}H_{25}ClN_4OS$ | | | |
|---|---|---|---|
| | C | H | N |
| Calcd. | 62.64 | 5.71 | 12.70 |
| Found | 62.69 | 5.81 | 12.76 |

Example 15

A mixture of 4-chloromethyl-2-phenylthiazole monohydrochloride (2.46 g), 1-benzhydrylpiperazine (2.52 g) and potassium carbonate (1.4 g) in N,N-dimethylformamide (40 ml) was stirred at 70° C. for 2 hours. After the reaction mixture was poured into ice-water, it was extracted with ethyl acetate. The extract was washed with water, dried over anhydrous magnesium sulfate and then evaporated to give an oil of 4-(4-benzhydrylpiperazin-1-ylmethyl)-2-phenylthiazole, which was transformed into its hydrochloride in a conventional manner, followed by recrystallization from ethanol to obtain white crystals (2.7 g) of 4-(4-benzhydrylpiperazin-1-ylmethyl)-2-phenylthiazole dihydrochloride, mp 215°–218° C.

IR $cm^{-1}$ (Nujol): 3400, 1460, 1035, 780, 710.

NMR (DMSO-$d_6$): 3.1–4.0 (8H, m), 4.58 (2H, s), 5.70 (1H, broad), 7.1–7.6 (10H, m), 7.6–8.1 (8H, m).

| Elemental Analysis: $C_{27}H_{27}N_3S.2HCl.\frac{1}{4}H_2O$ | | | |
|---|---|---|---|
| | C | H | N | $H_2O$ |
| Calcd. | 64.47 | 5.82 | 8.35 | 0.89 |
| Found | 64.27 | 6.19 | 8.01 | 0.77 |

Example 16

(1) Hydrogen sulfide was introduced into a mixture of dimethylcyanamide (8.75 g), triethylamine (12.6 g) and pyridine (17.5 ml) at 60° C. for 2 hours. After addition of petroleum ether (25 ml), the solution was ice-cooled. The precipitated crystals were collected by filtration, washed with petroleum ether and then dried, followed by recrystallization from water to give crystals (7.6 g) of N,N-dimethylthiourea, mp 160°–160.5° C.

(2) A mixture of the above object compound (3.1 g), 1,3-dichloro-2-propanone (3.8 g) in methanol (150 ml) was stirred at ambient temperature for 4 hours. After concentration of the reaction mixture, the residue was extracted with ethyl acetate, followed by neutralization with an aqueous solution of sodium bicarbonate and washing with an aqueous solution of sodium chloride. After drying over anhydrous magnesium sulfate, the solvent was removed by evaporation to obtain 4-chloromethyl-2-dimethylaminothiazole (5.3 g).

(3) A mixture of 4-chloromethyl-2-dimethylaminothiazole (2.62 g), 1-benzhydrylpiperazine (3.74 g) and potassium carbonate (2.07 g) in N,N-dimethylformamide (30 ml) was stirred at 60° C. for 5 hours. After the reaction mixture was poured into ice-water, it was extracted with ethyl acetate. The extract was washed with water, dried over anhydrous magnesium sulfate and then evaporated to dryness to give an oily residue, which was chromatographed on silica gel (120 g) using a mixture of chloroform and methanol (97:3 by volume) as an eluent. The eluates containing the desired compound were collected and evaporated to give a brown oil (3.4 g), which was transformed into its fumarate in a conventional manner, followed by recrystallization from a mixture of ethanol and diethyl ether to obtain pale-yellow crystals (1.52 g) of 4-(4-benzhydrylpiperazin-1-ylmethyl)-2-dimethylaminothiazole monofumarate, mp 180°–183.5° C.

IR $cm^{-1}$ (Nujol): 1706, 1635, 1560, 1238, 1196, 966, 705.

NMR δppm (DMSO-$d_6$): 2.40 (4H, m), 2.66 (4H, m), 3.56 (2H, s), 4.32 (1H, s), 6.54 (1H, s), 6.62 (2H, s), 7.0–7.5 (10H, m), 10.22 (2H, broad s).

| Elemental Analysis: $C_{23}H_{28}N_4S.C_4H_4O_4$ | | | |
|---|---|---|---|
| | C | H | N |
| Calcd. | 63.76 | 6.34 | 11.02 |
| Found | 64.01 | 6.09 | 10.94 |

Example 17

A mixture of 4-chloromethyl-2-isopropylthiazole (3.51 g), 1-benzhydrylpiperazine (5.04 g) and potassium carbonate (1.52 g) in N,N-dimethylformamide (60 ml) was stirred at 60° C. for 2 hours. After the reaction mixture was poured into ice-water, it was extracted twice with ethyl acetate. The combined extracts were washed with water, dried over anhydrous magnesium sulfate and then evaporated to give an oil (9.5 g), which was chromatographed on silica gel (150 g) using chloroform and a mixture of chloroform and methanol (50:1 by volume) as an eluent. The eluates containing the desired compound were collected and evaporated to give a brown oil (6.9 g), which was transformed into its fumarate in a conventional manner, followed by recrystallization from ethanol to obtain white crystals (4.6 g) of 4-(4-benzyhydrylpiperazin-1-ylmethyl)-2-isopropylthiazole monofumarate, mp 202°–203.5° C.

IR $cm^{-1}$ (Nujol): 1700, 1640, 1580, 1450, 1365, 1250, 1195, 980, 760, 705.

NMR δppm (DMSO-$d_6$): 1.25 (6H, d, J=7 Hz), 2.1–2.75 (8H, m), 3.20 (1H, septet), 3.63 (2H, s), 4.25 (1H, s), 6.59 (1H, s), 7.05–7.55 (10H, m), 10.22 (2H, broad).

| Elemental Analysis: $C_{24}H_{29}N_3S \cdot C_4H_4O_4$ | | | |
|---|---|---|---|
|  | C | H | N |
| Calcd. | 66.25 | 6.55 | 8.28 |
| Found | 66.20 | 6.50 | 8.18 |

Example 18

To a solution of 2-amino-4-chloromethylthiazole monohydrochloride (1.85 g) in N,N-dimethylformamide (7 ml) and pyridine (2 ml) was added dropwise methanesulfonyl chloride (0.85 ml) with stirring, and the stirring was continued at ambient temperature for half an hour. After concentration of the reaction mixture, the concentrate was neutralized with an aqueous solution of sodium bicarbonate, followed by extraction with ethyl acetate. The extract was washed with water, dried and then evaporated to give a brown oil (1.4 g). A mixture of this oil, 1-benzhydrylpiperazine (1.5 g) and potassium carbonate (0.85 g) in N,N-dimethylformamide (10 ml) was stirred at 80° C. for 1.5 hours. After the reaction mixture was poured into ice-water, it was extracted with water, dried over anhydrous magnesium sulfate. Removal of the solvent gave an oil (2.0 g), which was chromatographed on silica gel (40 g) using a mixture of chloroform and methanol (10:1 by volume) as an eluent. The eluates containing the desired compound were collected and evaporated to give crystals, which were recrystallized from ethyl acetate to obtain yellow crystals (0.5 g) of 4-(4-benzhydrylpiperazin-1-ylmethyl)-2-[N-(N,N-dimethylamino)methyleneamino]thiazole, mp 148°–150° C.

IR cm$^{-1}$ (Nujol): 1610, 1450, 1090, 1010, 755, 715.

NMR δppm (DMSO-d$_6$): 2.4–2.6 (8H, m), 2.86 (3H, s), 3.00 (3H, s), 3.33 (2H, s), 4.21 (1H, s), 6.63 (1H, s), 7.05–7.50 (10H, m), 8.16 (1H, s).

| Elemental Analysis: $C_{24}H_{29}N_5S$ | | | |
|---|---|---|---|
|  | C | H | N |
| Calcd. | 68.71 | 6.96 | 16.69 |
| Found | 68.91 | 7.12 | 16.45 |

Example 19

A mixture of 2-acetamido-4-(4-benzhydrylpiperazin-1-ylmethyl)thiazole (4.6 g), methanol (80 ml) and conc. hydrochloric acid (20 ml) was refluxed under heating for 3 hours with stirring. After concentration of the reaction mixture, the concentrate was neutralized with an aqueous solution of sodium bicarbonate, followed by extraction with ethyl acetate. The extract was washed with water, dried over anhydrous magnesium sulfate and then evaporated to give an amorphous product (4.0 g), which was chromatographed on silica gel using a mixture of ethyl acetate and methanol (10:1 by volume) as an eluent. The eluates containing the desired compound were collected and evaporated to give crystals, which were recrystallized from a mixture of ethyl acetate and diethyl ether to obtain white crystals (2.6 g) of 2-amino-4-(4-benzhydrylpiperazin-1-ylmethyl)thiazole, mp 156°–160° C.

IR cm$^{-1}$ (Nujol): 3400, 3250, 1600, 1515, 1020, 760.

NMR δppm (DMSO-d$_6$): 2.41 (8H, m), 3.30 (2H, s), 4.32 (1H, s), 6.25 (1H, s), 6.80 (2H, s), 7.30 (10H, m).

| Elemental Analysis: $C_{21}H_{24}N_4S$ | | | |
|---|---|---|---|
|  | C | H | N |
| Calcd. | 69.20 | 6.63 | 15.37 |
| Found | 69.25 | 6.56 | 15.43 |

Example 20

2-Amino-4-[4-(4-chlorobenzhydryl)piperazin-1-ylmethyl]thiazole (4.1 g) was obtained by hydrolyzing 2-acetamido-4-[4-(4-chlorobenzhydryl)piperazin-1-ylmethyl]thiazole (6.0 g) with conc.hydrochloric acid (10 ml) according to a similar manner to that of Example 19.

IR cm$^{-1}$ (Nujol): 3230, 3100, 1640, 1535, 1135.

NMR δppm (DMSO-d$_6$): 2.3–2.6 (8H, m), 3.32 (2H, s), 4.23 (1H, s), 6.21 (1H, s), 6.85 (2H, s), 7.1–7.4 (9H, m).

| Elemental Analysis: $C_{21}H_{23}ClN_4S$ | | | |
|---|---|---|---|
|  | C | H | N |
| Calcd. | 63.21 | 5.81 | 14.04 |
| Found | 63.48 | 5.83 | 13.65 |

Example 21

A mixture of 2-acetamido-4-[2-(4-benzhydrylpiperazin-1-yl)ethyl]thiazole (3.75 g), methanol (26 ml) and conc. hydrochloric acid (13 ml) was refluxed under heating for 2.5 hours. After concentration of the reaction mixture, the concentrate was recrystallized from methanol to obtain white crystals (3.4 g) of 2-amino-4-[2-(4-benzhydrylpiperazin-1-yl)ethyl]thiazole trihydrochloride, mp 188°–190° C.

IR cm$^{-1}$ (Nujol): 1645, 1460, 1380, 920, 710.

NMR δppm (DMSO-d$_6$): 2.9–3.9 (14H, m), 5.8 (1H, broad), 6.78 (1H, s), 7.2–7.6 (6H, m), 7.8–8.1 (4H, m), 8.2–10.1 (3H, broad).

| Elemental Analysis: $C_{22}H_{26}N_4S \cdot 3HCL \cdot \frac{1}{2}H_2O$ | | | | |
|---|---|---|---|---|
|  | C | H | N | $H_2O$ |
| Calcd. | 53.16 | 6.08 | 11.27 | 1.81 |
| Found | 53.24 | 6.48 | 11.29 | 1.56 |

Example 22

2-Amino-4-[2-{4-(4-chlorobenzhydryl)piperazin-1-yl}ethyl]thiazole trihydrochloride (2.65 g) was obtained by hydrolyzing 2-acetamido-4-[2-{4-(4-chlorobenzhydryl)piperazin-1-yl}ethyl]thiazole (5.0 g) with conc. hydrochloric acid (10 ml) according to a similar manner to that of Example 21, mp 180°–185° C. (dec.).

IR cm$^{-1}$ (Nujol): 3210, 3050, 2700–2300, 1640, 1605, 765, 725.

NMR δppm (DMSO-d$_6$): 3.2–3.7 (12H, broad), 5.81 (1H, broad), 6.85 (1H, s), 7.4–7.9 (9H, m), 9.20 (5H, broad).

| Elemental Analysis: $C_{22}H_{25}ClN_4S \cdot 3HCl \cdot \frac{1}{2}H_2O$ | | | | |
|---|---|---|---|---|
|  | C | H | N | $H_2O$ |
| Calcd. | 50.15 | 5.39 | 10.63 | 0.54 |
| Found | 49.77 | 5.92 | 10.06 | 0.62 |

Example 23

A mixture of 2-acetamido-4-[3-(4-benzhydrylpiperazin-1-yl)propyl]thiazole (1.2 g), methanol (25 ml) and conc. hydrochloric acid (6 ml) was refluxed under heating for 5 hours. After concentration of the reaction mixture, the resultant crystals were recrystallized from a mixture of methanol and diethyl ether to obtain white crystals (1.05 g) of 2-amino-4-[3-(4-benzhydrylpiperazin-1-yl)propyl]thiazole trihydrochloride, mp 205°–215° C.

IR cm$^{-1}$ (Nujol): 3400, 3200, 2800–2400, 1620, 1580.

NMR δppm (DMSO-d$_6$): 2.01 (2H, broad), 2.62 (2H, broad), 3.30 (6H, broad), 3.75 (4H, broad), 5.80 (1H, broad), 6.74 (1H, s), 7.45 (10H, m), 7.95 (5H, broad).

| Elemental Analysis: $C_{23}H_{28}N_4S \cdot 3HCl \cdot H_2O$ | | | |
|---|---|---|---|
| | C | H | N | H$_2$O |
| Calcd. | 53.13 | 6.40 | 10.78 | 3.47 |
| Found | 53.58 | 6.57 | 10.72 | 3.19 |

Example 24

A mixture of 2-acetamido-4-(4-benzhydrylpiperazin-1-ylmethyl)-5-chlorothiazole (5.4 g), methanol (50 ml) and conc. hydrochloric acid (12.5 ml) was refluxed under heating for 6 hours. After concentration of the reaction mixture, the resultant crystals were recrystallized from methanol to obtain white crystals (1.3 g) of 2-amino-4-(4-benzhydrylpiperazin-1-ylmethyl)-5-chlorothiazole trihydrochloride, mp 210°–250° C.

IR cm$^{-1}$ (Nujol): 3600, 3450, 2800–2400, 1640, 1580.

NMR δppm (DMSO-d$_6$): 3.5–3.7 (8H, m), 4.20 (2H, s), 5.95 (1H, broad), 7.0–7.4 (3H, broad), 7.40–7.95 (10H, m).

| Elemental Analysis: $C_{21}H_{23}ClN_4S \cdot 3HCl$ | | | |
|---|---|---|---|
| | C | H | N |
| Calcd. | 49.61 | 5.15 | 11.02 |
| Found | 49.59 | 5.12 | 10.93 |

Example 25

To a solution of 2-amino-4-(4-benzhydrylpiperazin-1-ylmethyl)thiazole (1.82 g) and triethylamine (1.4 ml) in chloroform (18 ml) was added dropwise methanesulfonyl chloride (0.78 ml) under ice-cooling with stirring, and the stirring was continued at the same temperature for 1.25 hours. After concentration of the reaction mixture, the residue was neutralized with an aqueous solution of sodium bicarbonate, followed by extraction with ethyl acetate. The extract was washed with water, dried over anhydrous magnesium sulfate and then evaporated to give an amorphous product (2.2 g), which was chromatographed on silica gel (40 g) using a mixture of chloroform and methanol (50:1 by volume) as an eluent. The eluates containing the desired compound were collected and then evaporated to give crystals, which were recrystallized from ethyl acetate to give white crystals (0.65 g) of 4-(4-benzhydrylpiperazin-1-ylmethyl)-2-methanesulfonamidothiazole, mp 177°–179° C.

IR cm$^{-1}$ (Nujol): 3170, 1610, 1530, 1445, 1265, 1125, 770, 700.

NMR δppm (DMSO-d$_6$): 2.4–2.8 (8H, m), 2.91 (3H, s), 3.43 (2H, s), 4.38 (1H, s), 6.71 (1H, s), 7.2–7.8 (10H, m), 9.50 (1H, broad).

| Elemental Analysis: $C_{22}H_{26}N_4O_2S_2$ | | | |
|---|---|---|---|
| | C | H | N |
| Calcd. | 59.70 | 5.92 | 12.66 |
| Found | 59.72 | 5.84 | 12.70 |

The eluates obtained from the other part was evaporated to dryness to give a residue, which was recrystallized from a mixture of chloroform and diethyl ether to obtain 4-(4-benzhydrylpiperazin-1-ylmethyl)-2-(N,N-dimesylamino)thiazole (0.47 g), mp 167°–168° C.

IR cm$^{-1}$ (Nujol): 1600, 1595, 1370, 1160, 760, 710.

NMR δppm (DMSO-d$_6$): 2.15–2.55 (8H, broad), 3.56 (8H, s), 4.39 (1H, s), 7.05–7.5 (10H, m), 7.59 (1H, s).

| Elemental Analysis: $C_{23}H_{28}N_4O_4S_3$ | | | |
|---|---|---|---|
| | C | H | N |
| Calcd. | 53.05 | 5.42 | 10.76 |
| Found | 53.17 | 5.37 | 10.64 |

Example 26

To a solution of 2-amino-4-(4-benzhydrylpiperazin-1-ylmethyl)thiazole (1.8 g) and triethylamine (1.4 ml) in chloroform (15 ml) was added dropwise ethanesulfonyl chloride (1.28 g) under ice-cooling with stirring, and the stirring was continued at the same temperature for 45 minutes and at ambient temperature for additional 2.5 hours. After concentration of the reaction mixture, the residue was neutralized with an aqueous solution of sodium bicarbonate, followed by extraction with ethyl acetate. The extract was washed with water, dried over anhydrous magnesium sulfate and then evaporated to give an oil (3 g), which was chromatographed on silica gel (90 g) using a mixture of chloroform and methanol (50:1 by volume) as an eluent. The eluates containing the desired compound were collected and then evaporated to give an amorphous product, which was recrystallized from ethyl acetate to give crystals (1.2 g) of 4-(4-benzhydrylpiperazin-1-ylmethyl)-2-ethanesulfonamidothiazole, mp 159°–160.5° C.

IR cm$^{-1}$ (Nujol): 3080, 1612, 1558, 1448, 1318, 1300, 1135.

NMR δppm (DMSO-d$_6$): 1.15 (3H, t, J=7.0 Hz), 2.1–2.6 (8H, m), 2.94 (2H, q, J=7.0 Hz), 3.32 (2H, s), 4.26 (1H, s), 6.47 (1H, s), 7.0–7.6 (10H, m), 8.0–9.5 (1H, broad).

| Elemental Analysis: $C_{23}H_{28}N_4O_2S_2$ | | | |
|---|---|---|---|
| | C | H | N |
| Calcd. | 60.50 | 6.18 | 12.27 |
| Found | 60.89 | 6.11 | 12.22 |

Example 27

To a solution of 2-amino-4-(4-benzhydrylpiperazin-1-ylmethyl)thiazole (1.8 g) and triethylamine (1.4 ml) in chloroform (15 ml) was added dropwise propanesulfonyl chloride (1.42 g) under ice-cooling with stirring, and the stirring was continued at the same temperature for 70 minutes. After concentration of the reaction mixture, the residue was neutralized with an aqueous solution of sodium bicarbonate, followed by extraction with ethyl acetate. The extract was washed with water, dried over anhydrous magnesium sulfate and then evaporated to give an oil (2.9 g), which was chromatographed on silica gel (30 g) using a mixture of chloroform and methanol (50:1 by volume) as an eluent. The eluates containing the desired compound were collected and then evaporated to give a foamy product, which was recrystallized from ethyl acetate to give white crystals (0.9 g) of 4-(4-benzhydrylpiperazin-1-ylmethyl)-2-propanesulfonamidothiazole, mp 165°–167° C.

IR cm$^{-1}$ (Nujol): 3220, 1540, 1275, 1220, 1000, 887, 708.

NMR δppm (DMSO-d$_6$): 0.95 (3H, t, J=7.0 Hz), 1.68 (2H, m), 2.1–2.8 (8H, m), 2.98 (2H, t, J=7.0 Hz), 3.36 (2H, s), 4.31 (1H, s), 6.53 (1H, s), 7.1–7.8 (10H, m), 7.8–8.0 (1H, broad).

| Elemental Analysis: C$_{24}$H$_{30}$N$_4$O$_2$S$_2$ | | | |
|---|---|---|---|
| | C | H | N |
| Calcd. | 61.25 | 6.42 | 11.90 |
| Found | 61.20 | 6.41 | 11.80 |

Example 28

4-(4-Benzhydrylpiperazin-1-ylmethyl)-2-n-butanesulfonamidothiazole (1.8 g) was obtained by reacting 2-amino-4-(4-benzhydrylpiperazin-1-ylmethyl)thiazole (2.73 g) with n-butanesulfonyl chloride (2.35 g) according to a similar manner to that of Example 27, mp 185°–187° C.

IR cm$^{-1}$ (Nujol): 3200, 1524, 1260, 1118, 1030, 880, 708.

NMR δppm (DMSO-d$_6$): 0.83 (3H, m), 1.0–2.0 (4H, m), 2.37 (8H, m), 2.75–3.2 (2H, m), 3.33 (2H, s), 4.26 (1H, s), 6.49 (1H, s), 7.1–7.55 (10H, m), 8.0–11.0 (1H, broad s).

| Elemental Analysis: C$_{25}$H$_{32}$N$_4$O$_2$S$_2$ | | | |
|---|---|---|---|
| | C | H | N |
| Calcd. | 61.95 | 6.65 | 11.56 |
| Found | 61.82 | 6.62 | 11.54 |

Example 29

To a solution of 2-amino-4-(4-benzhydrylpiperazin-1-ylmethyl)thiazole (1.1 g) in tetrahydrofuran (10 ml) and pyridine (5 ml) was added dropwise propionyl chloride (0.92 ml) under ice-cooling with stirring, and the stirring was continued at the same temperature for an hour. After concentration of the reaction mixture the residue was extracted with ethyl acetate, followed by washing with an aqueous solution of sodium bicarbonate and water and drying over anhydrous magnesium sulfate. Removal of the solvent gave an oil, which was transformed into its hydrochloride in a conventional manner, followed by recrystallization from a mixture of methanol and diethyl ether to obtain white crystals (0.8 g) of 4-(4-benzhydrylpiperazin-1-ylmethyl)-2-propionamidothiazole dihydrochloride, mp 181°–184° C. (dec.).

IR cm$^{-1}$ (Nujol): 3380, 2400, 1680, 1540, 710.

NMR δppm (DMSO-d$_6$): 1.05 (3H, t), 2.51 (2H, q,) 3.18 (4H, broad), 3.61 (4H, broad), 4.46 (2H, s), 5.58 (1H, broad), 7.5–7.8 (12H, m), 13.05 (1H, s).

| Elemental Analysis: C$_{24}$H$_{28}$N$_4$OS.2HCl | | | |
|---|---|---|---|
| | C | H | N |
| Calcd. | 58.41 | 6.13 | 11.35 |
| Found | 58.12 | 6.52 | 10.80 |

Example 30

4-(4-Benzhydrylpiperazin-1-ylmethyl)-2-butyramidothiazole (0.55 g) was obtained by reacting 2-amino-4-(4-benzhydrylpiperazin-1-ylmethyl)thiazole (1.1 g) with butyryl chloride (0.93 ml) according to a similar manner to that of Example 29, mp 128°–135° C.

IR cm$^{-1}$ (Nujol): 3180, 1695, 1570, 1560, 705.

NMR δppm (DMSO-d$_6$): 0.9 (3H, t), 1.61 (2H, m), 2.43 (10H, m), 3.49 (2H, s), 4.18 (1H, s), 6.85 (1H, s), 7.10 (10H, m), 11.95 (1H, s).

| Elemental Analysis: C$_{25}$H$_{30}$N$_4$OS | | | |
|---|---|---|---|
| | C | H | N |
| Calcd. | 69.10 | 6.96 | 12.89 |
| Found | 68.68 | 7.48 | 12.76 |

Example 31

4-(4-Benzhydrylpiperazin-1-ylmethyl)-2-isobutyramidothiazole (0.4 g) was obtained by reacting 2-amino-4-(4-benzhydrylpiperazin-1-ylmethyl)thiazole (1.1 g) with isobutyryl chloride (0.8 g) according to a similar manner to that of Example 29, mp 132°–140° C.

IR cm$^{-1}$ (Nujol): 3170, 1695, 1560, 1105, 710.

NMR δppm (DMSO-d$_6$): 1.05 (3H, s), 1.20 (3H, s), 2.4–2.5 (9H, m), 3.50 (2H, s), 4.15 (1H, s), 6.94 (1H, s), 7.33 (10H, m), 12.8 (1H, s).

| Elemental Analysis: C$_{25}$H$_{30}$N$_4$OS | | | |
|---|---|---|---|
| | C | H | N |
| Calcd. | 69.10 | 6.96 | 12.89 |
| Found | 68.48 | 7.42 | 12.72 |

Example 32

2-Benzamido-4-(4-benzhydrylpiperazin-1-ylmethyl)thiazole dihydrochloride (1.1 g) was obtained by reacting 2-amino-4-(4-benzhydrylpiperazin-1-ylmethyl)thiazole (1.8 g) with benzoyl chloride (1.4 ml) according to a similar manner to that of Example 29, mp 195°–200° C. (dec.).

IR cm$^{-1}$ (Nujol): 3300, 2500–2400, 1655, 1550, 710.

NMR δppm (DMSO-d$_6$): 3.25 (4H, broad), 3.70 (4H, broad), 4.45 (2H, s), 5.60 (1H, broad), 7.3–8.0 (18H, m).

Example 33

2-(p-Anisoylamino)-4-(4-benzhydrylpiperazin-1-ylmethyl)thiazole dihydrochloride (0.65 g) was obtained by reacting 2-amino-4-(4-benzhydrylpiperazin-1-ylmethyl)thiazole (1.1 g) with p-anisoyl chloride (1.3 g) according to a similar manner to that of Example 29, mp 175°–190° C.

IR cm$^{-1}$ (Nujol): 3400, 2500, 1660, 1600, 710.

NMR δppm (DMSO-d$_6$): 3.25 (4H, broad), 3.65 (4H, broad), 3.93 (3H, s), 4.45 (2H, s), 5.51 (1H, broad), 7.8–8.0 (16H, m), 13.4 (1H, s).

EXAMPLE 34

4-(4-Benzhydrylpiperazin-1-ylmethyl)-2-cyclohexylcarboxamidothiazole dihydrochloride (0.8 g) was obtained by reacting 2-amino-4-(4-benzhydrylpiperazin-1-ylmethyl)thiazole (1.1 g) with cyclohexylcarbonyl chloride (1.68 ml) according to a similar manner to that of Example 29, mp 200°–207° C.

IR cm$^{-1}$ (Nujol): 3450, 3100, 2400, 1670, 1550, 710.

NMR δppm (DMSO-d$_6$): 1.2–1.9 (10H, broad), 3.2–3.6 (8H, broad), 4.35 (2H, s), 5.51 (1H, broad), 7.4–7.8 (12H, m), 12.10 (1H, s).

| Elemental Analysis: C$_{28}$H$_{34}$N$_4$OS.2HCl.½H$_2$O | | | |
|---|---|---|---|
| | C | H | N | H$_2$O |
| Cald. | 60.43 | 6.65 | 10.07 | 1.61 |
| Found | 60.02 | 6.74 | 10.00 | 1.56 |

EXAMPLE 35

The solution of 2-amino-4-(4-benzhydrylpiperazin-1-ylmethyl)thiazole (1.1 g) and methyl isocyanate (0.54 ml) in chloroform (10 ml) was refluxed for 2 hours. After concentration of the reaction mixture, the residue was extracted with ethyl acetate, followed by washing with an aqueous solution of sodium bicarbonate and water, drying over anhydrous magnesium sulfate and then evaporating to dryness to give an amorphous product (1.4 g), which was chromatographed on silica gel (about 30 g) using a mixture of chloroform and methanol (50:1 by volume) as an eluent. The eluates containing the desired compound were collected and evaporated to give a residue, which was transformed into its fumarate in a conventional manner, followed by recrystallization from a mixture of ethanol and diethyl ether to obtain white crystals (0.38 g) of 4-(4-benzhydrylpiperazin-1-ylmethyl)-2-(3-methylureido)thiazole monofumarate, mp 188°–191° C.

IR cm$^{-1}$ (Nujol): 3440, 3300, 2400, 1675, 1635, 1565, 760, 705.

NMR δppm (DMSO-d$_6$): 2.5–2.7 (11H, m), 3.56 (2H, s), 4.33 (1H, s), 6.50–7.00 (2H, broad), 6.66 (2H, s), 6.79 (1H, s), 7.1–7.7 (10H, m).

| Elemental Analysis: C$_{23}$H$_{27}$N$_5$OS.C$_4$H$_4$O$_4$.4/5H$_2$O | | | |
|---|---|---|---|
| | C | H | N | H$_2$O |
| Calcd. | 58.75 | 5.94 | 12.68 | 2.61 |
| Found | 59.14 | 5.87 | 12.84 | 2.45 |

EXAMPLE 36

To a solution of 2-amino-4-(4-benzhydrylpiperazin-1-ylmethyl)thiazole (1.8 g) in tetrahydrofuran (5 ml) and pyridine (10 ml) was added dropwise ethoxalyl chloride (1.1 g) under ice-cooling with stirring, and the stirring was continued at the same temperature for an hour. After concentration of the reaction mixture, the residue was extracted with ethyl acetate, washed with water, dried over anhydrous magnesium sulfate and then evaporated to dryness to give a residue, which was chromatographed on silica gel using ethyl acetate as an eluent. The eluates containing the desired compound were collected and evaporated, followed by recrystallization from a mixture of ethyl acetate and n-hexane to obtain pale yellow crystals (0.7 g) of 4-(4-benzhydrylpiperazin-1-ylmethyl)-2-ethoxalylaminothiazole, mp 125°–128° C.

IR cm$^{-1}$ (Nujol): 3150, 1745, 1700, 1550, 760.

NMR δppm (DMSO-d$_6$): 1.31 (3H, t, 2.60 (8H, m), 3.61 (2H, s), 4.25 (1H, s), 4.30 (2H, q), 7.10 (1H, s), 7.3–7.6 (10H, m).

| Elemental Analysis: C$_{25}$H$_{28}$N$_4$O$_3$S | | | |
|---|---|---|---|
| | C | H | N |
| Calcd. | 64.63 | 6.07 | 12.06 |
| Found | 65.13 | 6.45 | 11.42 |

EXAMPLE 37

To a solution of 2-amino-4-[2-(4-benzhydrylpiperazin-1-yl)ethyl]thiazole (1.7 g) and triethylamine (1.26 ml) in chloroform (17 ml) was added dropwise methanesulfonyl chloride (1028 mg) under cooling with stirring, and the stirring was continued at the same temperature for 2.7 hours. After concentration of the reaction mixture, the residue was neutralized with an aqueous solution of sodium bicarbonate, followed by extraction with ethyl acetate. The extract was washed with water, dried over anhydrous magnesium sulfate and then evaporated to give an amorphous product (2.5 g), which was chromatographed on silica gel (60 g) using a mixture of chloroform and methanol (50:1 by volume) as an eluent. The eluates containing a desired compound were collected and evaporated to give an oil, which was transformed into its hydrochloride in a conventional manner, followed by recrystallization from methanol to obtain white crystals (1.2 g) of 4-[2-(4-benzhydrylpiperazin-1-yl)ethyl]-2-methanesulfonamidothiazole dihydrochloride, mp 190°–205° C.

IR cm$^{-1}$ (Nujol): 3400, 2400, 1605, 1520, 1300, 1130, 705.

NMR δppm (DMSO-d$_6$): 2.85 (3H, s), 3.0–3.75 (12H, m), 5.50 (1H, broad), 6.53 (1H, s), 7.2–7.9 (10H, m).

| Elemental Analysis: C$_{23}$H$_{28}$N$_4$O$_2$S$_2$.2HCl.½H$_2$O | | | |
|---|---|---|---|
| | C | H | N | H$_2$O |
| Calcd. | 51.39 | 5.81 | 10.42 | 1.67 |
| Found | 51.15 | 5.62 | 10.43 | 1.20 |

Example 38

To a solution of 2-amino-4-[3-(4-benzhydrylpiperazin-1-yl)propyl]thiazole (0.9 g) and triethylamine (0.64 ml) in chloroform (9 ml) was added dropwise methanesulfonyl chloride (520 mg) under cooling with stirring, and the stirring was continued at the same temperature for 2 hours and then at ambient temperature overnight. After concentration of the reaction mixture, the residue was neutralized with an aqueous solution of sodium bicarbonate, followed by extraction with ethyl acetate. The extract was washed with water, dried over anhydrous magnesium sulfate and then evaporated to give an oil (1.3 g), which was chromatographed on silica gel (30 g) using a mixture of chloroform and methanol (50:1 by volume) as an eluent. The eluates containing a desired compound were collected and evaporated to give crystals (0.75 g), which were recrystallized from ethyl acetate to give yellow crystals (0.41 g) of 4-[3-(4-benzhydrylpiperazin-1-yl)propyl]-2-methanesulfonamidothiazole, mp 181°–183° C.

IR cm$^{-1}$ (Nujol): 3550, 1540, 1460, 1275, 1120, 760, 705.

NMR δppm (DMSO-d$_6$): 1.73 (2H, m), 2.25–2.70 (12H, m), 2.86 (3H, s), 4.32 (1H, s), 5.30 (1H, broad), 6.36 (1H, s), 7.2–7.6 (10H, m).

| Elemental Analysis: C$_{24}$H$_{30}$N$_4$O$_2$S$_2$ | | | |
|---|---|---|---|
| | C | H | N |
| Calcd. | 61.24 | 6.42 | 11.90 |
| Found | 61.58 | 6.39 | 11.90 |

Example 39

4-[3-(4-Benzhydrylpiperazin-1-yl)propyl]-2-ethanesulfonamidothiazole (0.9 g) was obtained by reacting 2-amino-4-[3-(4-benzhydrylpiperazin-1-yl)propyl]thiazole (2.0 g) with ethanesulfonyl chloride (1.28 g) according to a similar manner to that of Example 38, mp 162°–164° C.

IR cm$^{-1}$ (Nujol): 1460, 1370, 1290, 1263, 1115, 985, 747, 720.

NMR δppm (DMSO-d$_6$): 1.17 (3H, t, J=8.0 Hz), 1.4–2.7 (14H, m), 2.97 (2H, q, J=8.0 Hz), 4.30 (1H, s), 6.34 (1H, s), 7.1–7.6 (10H, m).

| Elemental Analysis: C$_{25}$H$_{32}$N$_4$O$_2$S$_2$ | | | |
|---|---|---|---|
| | C | H | N |
| Calcd. | 61.95 | 6.65 | 11.56 |
| Found | 62.38 | 6.65 | 11.61 |

Example 40

To a solution of 2-amino-4-(4-benzhydrylpiperazin-1-ylmethyl)-5-chlorothiazole (3.2 g) in tetrahydrofuran (20 ml) and pyridine (10 ml) was added dropwise ethoxalyl chloride (2.2 g) under ice-cooling with stirring, and the stirring was continued at the same temperature for an hour. After concentration of the reaction mixture, the residue was extracted with ethyl acetate, followed by adding 10% hydrochloric acid. The separated aqueous solution was neutralized with an aqueous solution of sodium bicarbonate and then extracted with ethyl acetate. The extract was washed with water, dried over anhydrous magnesium sulfate and then evaporated to dryness to give an amorphous product (3.0 g), which was chromatographed on silica gel (50 g) using a mixture of chloroform and methanol (50:1 by volume) as an eluent. The eluates containing the desired compound were collected and evaporated to give crystals, which were recrystallized from a mixture of chloroform and diethyl ether to obtain yellow crystals (0.8 g) of 4-(4-benzhydrylpiperazin-1-ylmethyl)-5-chloro-2-ethoxalylaminothiazole, mp 154°–156° C.

IR cm$^{-1}$ (Nujol): 3070, 1710, 1595, 1240.

NMR δppm (DMSO-d$_6$): 1.31 (3H, t), 2.29 (4H, m), 2.61 (4H, m), 3.65 (2H, s), 4.20 (2H, q), 4.18 (1H, s), 7.35–7.60 (10H, m).

| Elemental Analysis: C$_{25}$H$_{27}$ClN$_4$O$_3$S | | | |
|---|---|---|---|
| | C | H | N |
| Calcd. | 60.17 | 5.45 | 11.23 |
| Found | 60.05 | 5.33 | 11.17 |

Example 41

To a solution of 2-amino-4-[2-(4-benzhydrylpiperazin-1-yl)ethylthiomethyl]thiazole (1.5 g) in tetrahydrofuran (50 ml) and pyridine (15 ml) was added dropwise acetyl chloride (1.1 ml) under ice-cooling with stirring, and the stirring was continued at the same temperature for an hour. After concentration of the reaction mixture, the residue was extracted with ethyl acetate. The extract was washed with an aqueous solution of sodium bicarbonate and water, dried over anhydrous magnesium sulfate, and then evaporated to give an amorphous product (1.7 g), which was chromatographed on silica gel (20 g) using a mixture of chloroform and methanol (20:1 by volume) as an eluent. The eluates containing the desired compound were collected and evaporated to give a residue, which was transformed into fumarate in a conventional manner. Recrystallization from ethanol gave pale yellow crystals (1.5 g) of 2-acetamido-4-[2-(4-benzhydrylpiperazin-1-yl)ethylthiomethyl]thiazole monofumarate, mp 225°–227° C.

IR cm$^{-1}$ (Nujol): 3300, 2400, 1695, 1685, 1540, 760.

NMR δppm (DMSO-d$_6$): 2.10 (3H, s), 2.3–2.5 (8H, broad), 3.75 (2H, s), 4.30 (1H, s), 6.00 (5H, broad), 6.75 (2H, s), 7.0 (1H, s), 7.2–7.5 (10H, m).

| Elemental Analysis: C$_{25}$H$_{30}$N$_4$OS$_2$·C$_4$H$_4$O$_4$ | | | |
|---|---|---|---|
| | C | H | N |
| Calcd. | 59.77 | 5.88 | 9.61 |
| Found | 59.79 | 5.79 | 9.59 |

Example 42

A mixture of 2-acetamido-5-[2-(4-benzhydrylpiperazin-1-yl)ethyl]-4-methylthiazole (2.1 g), conc. hydrochloric acid (12 ml) and methanol (50 ml) was refluxed under heating for 5 hours. After concentration of the reaction mixture, the residue was neutralized with an aqueous solution of sodium bicarbonate, followed by extraction with ethyl acetate. The extract was washed with water, dried over anhydrous magnesium sulfate and then evaporated to give an amorphous product (2.0 g). To the solution of this amorphous product and triethylamine (1.34 ml) in chloroform (20 ml) was added dropwise mesyl chloride (0.74 ml) under ice-cooling with stirring, and the stirring was continued at the same temperature for 1.8 hours. The reaction mixture was washed with water, dried over anhydrous magnesium sulfate and then evaporated to give an oil (2.5 g), which was chromatographed on silica gel (50 g) using a mixture of chloroform and methanol (50:1 by volume) as an eluent. The eluates containing the desired compound were collected and evaporated to give an oil (2.0 g), which was transformed into its hydrochloride in a conventional manner, followed by recrystallization from methanol to obtain white crystals (1.4 g) of 5-[2-(4-benzhydrylpiperazin-1-yl)ethyl]-2-methanesulfonamido-4-methylthiazole trihydrochloride, mp 195°–205° C.

IR cm$^{-1}$ (Nujol): 3450, 1635, 1540, 1275, 1125, 760.

NMR δppm (DMSO-d$_6$): 2.16 (3H, s), 2.92 (3H, s), 3.2–3.8 (12H, broad), 5.63 (1H, broad), 7.3–7.9 (10H, m).

Example 43

S-(2-Aminothiazol-4-ylmethyl)isothiourea dihydrochloride (2.6 g) and 4-benzhydryl-1-(2-chloroethyl)piperazine (3.87 g) were suspended in ethanol (50 ml) in a stream of nitrogen, and thereto was added at a time water (30 ml) containing sodium hydroxide (2.8 g) at ambient temperature with stirring, and the stirring was continued at 50° C. for half an hour. The precipitated crystals were collected by filtration, washed with ethanol and then recrystallized from methanol to give pale yellow crystals (3.0 g) of 2-amino-4-[2-(4-benzhydryl-piperazin-1-yl)ethylthiomethyl]thiazole, mp 159°–161° C.

IR cm$^{-1}$ (Nujol): 3300, 3100, 1670, 1530, 760, 710.

NMR δppm (DMSO-d$_6$): 2.60 (12H, m), 3.50 (2H, s), 4.21 (1H, s), 6.25 (1H, s), 6.90 (2H, s), 7.3–7.6 (10H, m).

| Elemental Analysis: C$_{23}$H$_{28}$N$_4$S$_2$ | | | |
|---|---|---|---|
| | C | H | N |
| Calcd. | 65.05 | 6.64 | 13.19 |
| Found | 64.97 | 6.68 | 13.05 |

Example 44

To a suspension of 4-(4-benzhydrylpiperazin-1-ylmethyl)-2-methanesulfonamidothiazole (1.37 g) in water (31 ml) and methanol (80 ml) was added 0.1 N aqueous solution of sodium hydroxide (31 ml) with stirring, followed by warming the reaction mixture for dissolving it. After concentration of the reaction mixture, the residual crystals were recrystallized from a mixture of methanol and water to obtain pale yellow crystals (1.1 g) of sodium salt of 4-(4-benzhydrylpiperazin-1-ylmethyl)-2-methanesulfonamidothiazole, mp 165°–175° C. (dec.).

IR cm$^{-1}$ (Nujol): 1590, 1440, 1260, 1120, 705.

NMR δppm (DMSO-d$_6$): 2.4–2.6 (8H, m), 2.71 (3H, s), 3.31 (2H, s), 4.33 (1H, s), 6.34 (1H, s), 7.3–7.6 (10H, m).

| Elemental Analysis: C$_{22}$H$_{25}$N$_4$O$_2$S$_2$Na.½H$_2$O | | | | | |
|---|---|---|---|---|---|
| | C | H | N | Na | H$_2$O |
| Calcd. | 55.91 | 5.54 | 11.86 | 4.86 | 1.90 |
| Found | 56.09 | 6.13 | 11.94 | 4.22 | 1.65 |

We claim:

1. A compound selected from the group consisting of 2-acetamido-4-(4-benzhydrylpiperazin-1-ylmethyl)-thiazole, 2-acetamido-4[2-(4-benzhydrylpiperazin-1-yl)ethyl]thiazole, 2-acetamino-4-[2-(4-(4-chlorobenzhydryl)-piperazin-1-yl)ethyl]thiazole, 2-acetamido-4-[3-(4-benzyhydrylpiperazin-1-yl)-propyl]thiazole, 2-acetamido-5-[2-(4-benzhydrylpiperazin-1-yl)ethyl]-4-methylthiazole, 4-(4-benzhydrylpiperazin-1-ylmethyl)-2-[N-(N,N-dimethylamino)-methyleneamino]thiazole, 2-amino-4-[4-benzhydrylpiperazin-1-ylmethyl]thiazole, 2-amino-4-[3-(4-benzhydrylpiperazin-1-yl)propyl]-thiazole, 4-[4-benzhydrylpiperazin-1-ylmethyl]-2-methanesulfonamidothiazole, 4-(4-benzhydrylpiperazin-1-ylmethyl)-2-(N,N-dimesylamino)-thiazole, 4-(4-benzhydrylpiperazin-1-ylmethyl)-2-ethanesulfonamido-thiazole, 4-[4-benzhydrylpiperazin-1-ylmethyl]-2-propanesulfonamidothiazole, 4-[2-(4-benzhydrylpiperazin-1-yl)ethyl]-2-methanesulfonamido-thiazole, 4-[3-(4-benzhydrylpiperazin-1-yl)propyl]-2-methanesulfonamido-thiazole, and 4-[3-(4-benzhydrylpiperazin-1-yl)propyl]-2-ethanesulfonamido-thiazole, and pharmaceutically acceptable salts thereof.

2. A compound of claim 1, which is 2-acetamido-4-(4-benzhydrylpiperazin-1-ylmethyl)thiazole and pharmaceutically acceptable salt thereof.

3. A compound of claim 1, which is 2-acetamido-4[2-(4-benzhydrylpiperazin-1-yl)ethyl]thiazole and pharmaceutically acceptable salt thereof.

4. A compound of claim 1 which is 2-acetamino-4-[2-(4-(4-chlorobenzhydryl)-piperazin-1-yl)ethyl]thiazole and pharmaceutically acceptable salts thereof.

5. A compound of claim 1, which is 2-acetamido-4-[3-(4-benzhydrylpiperazin-1-yl)-propyl]thiazole and pharmaceutically acceptable salts thereof.

6. A compound of claim 1, which is 2-acetamido-5-[2-(4-benzhydrylpiperazin-1-yl)ethyl]-4-methylthiazole and pharmaceutically acceptable salts thereof.

7. A compound of claim 1 which is 4-(4-benzhydrylpiperazin-1-ylmethyl)-2-[N-(N,N-dimethylamino)methyleneamino]thiazole and pharmaceutically acceptable salts thereof.

8. A compound of claim 1, which is 2-amino-4-[4-benzhydrylpiperazin-1-ylmethyl]thiazole and pharmaceutically acceptable salts thereof.

9. A compound of claim 1, which is 2-amino-4-[3-(4-benzhydrylpiperazin-1-yl)propyl]thiazole and pharmaceutically acceptable salts thereof.

10. A compound of claim 1, which is 4-[4-benzhydrylpiperazin-1-ylmethyl]-2-methanesulfonamido-thiazole and pharmaceutically acceptable salts thereof.

11. A compound of claim 1, which is 4-(4-benzhydrylpiperazin-1-ylmethyl)-2-(N,N-dimesylamino)-thiazole and pharmaceutically acceptable salts thereof.

12. A compound of claim 1, which is 4-(4-benzhydrylpiperazin-1-ylmethyl)-2-ethanesulfonamidothiazole and pharmaceutically acceptable salts thereof.

13. A compound of claim 1, which is 4-[4-benzhydrylpiperazin-1-ylmethyl]-2-propanesulfonamido-thiazole and pharmaceutically acceptable salts thereof.

14. A compound of claim 1, which is 4-[2-(4-benzhydrylpiperazin-1-yl)ethyl]-2-methanesulfonamido-thiazole and pharmaceutically acceptable salts thereof.

15. A compound of claim 1, which is 4-[3-(4-benzhydrylpiperazin-1-yl)propyl]-2-methanesulfonamido-thiazole and pharmaceutically acceptable salts thereof.

16. A compound of claim 1, which is 4-[3-(4-benzhydrylpiperazin-1-yl)propyl]-2-ethanesulfonamido-thiazole and pharmaceutically acceptable salts thereof.

17. An antiallergic pharmaceutical composition comprising a compound of claim 1, as an effective ingredient, in association with a pharmaceutically acceptable, substantially nontoxic carrier or excipient.

18. A method for treatment of allergic symptoms which comprises administering a compound of claim 1 to human beings or animals.

* * * * *

UNITED STATES PATENT AND TRADEMARK OFFICE
CERTIFICATE OF CORRECTION

PATENT NO. : 4,411,900

DATED : October 25, 1983

INVENTOR(S) : Ueda et al

It is certified that error appears in the above-identified patent and that said Letters Patent is hereby corrected as shown below:

Title should read as follows:

--[54] BENZHYDRYLPIPERAZINYL THIAZOLE DERIVATIVES AND PHARMACEUTICAL COMPOSITION COMPRISING THE SAME--

Signed and Sealed this

Thirty-first Day of January 1984

[SEAL]

Attest:

GERALD J. MOSSINGHOFF

Attesting Officer

Commissioner of Patents and Trademarks